(12) United States Patent
Rocamora et al.

(10) Patent No.: US 6,494,860 B2
(45) Date of Patent: Dec. 17, 2002

(54) INTRODUCER WITH MULTIPLE SHEATHS AND METHOD OF USE THEREFOR

(75) Inventors: Jose M. Rocamora, Imperial, CA (US); Thomas P Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 10 days.

(21) Appl. No.: 09/779,394

(22) Filed: Feb. 8, 2001

(65) Prior Publication Data

US 2002/0107482 A1 Aug. 8, 2002

(51) Int. Cl.[7] .............................................. A61M 25/00
(52) U.S. Cl. ..................... 604/43; 604/103.14; 604/161
(58) Field of Search ................................. 604/510, 161, 604/43, 264, 103.14

(56) References Cited

U.S. PATENT DOCUMENTS

| 4,406,656 A | * | 9/1983 | Hattler et al. ................. 604/43 |
| 4,512,351 A | | 4/1985 | Pohndorf |
| 4,687,469 A | | 8/1987 | Osypka |
| 4,738,666 A | * | 4/1988 | Fuqua .................... 604/103.14 |
| 5,106,368 A | * | 4/1992 | Uldall et al. ................... 604/43 |
| 5,256,150 A | | 10/1993 | Quiachon et al. |
| 5,397,311 A | | 3/1995 | Walker et al. .............. 604/160 |
| 5,472,418 A | | 12/1995 | Palestrant |
| 5,618,267 A | | 4/1997 | Palestrant |
| 5,951,518 A | | 9/1999 | Licata et al. ................. 604/161 |

FOREIGN PATENT DOCUMENTS

| DE | 3936811 A1 | 9/1990 |
| EP | 0 249 456 A2 | 12/1987 |

* cited by examiner

Primary Examiner—Philippe Derakshani
(74) Attorney, Agent, or Firm—Cummings & Lockwood LLC

(57) ABSTRACT

A vascular introducer is disclosed which includes an elongated primary sheath defining an interior lumen and having opposed proximal and distal end portions, and at least an elongated secondary sheath disposed within the interior lumen of the primary sheath and adapted for movement from a collapsed condition to an open condition in response to insertion of a dilator through an interior lumen thereof.

35 Claims, 7 Drawing Sheets

FIG_1
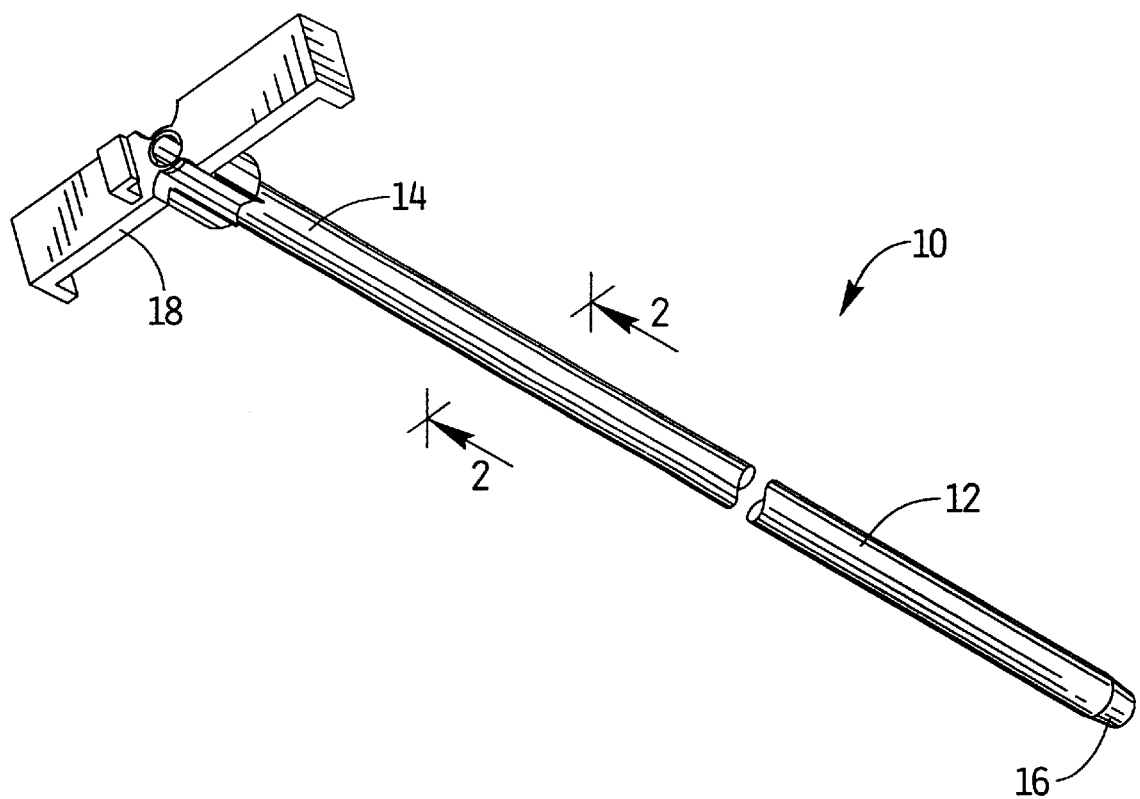
FIG_2
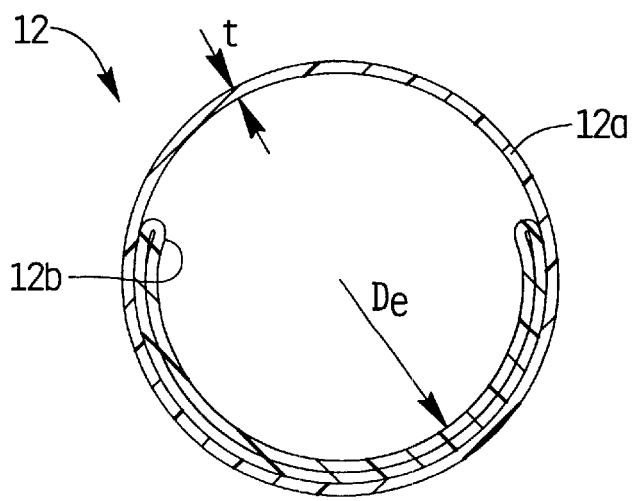

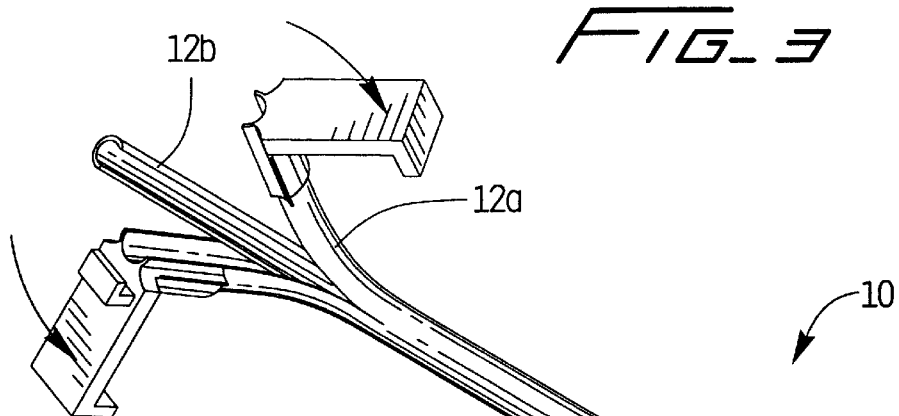
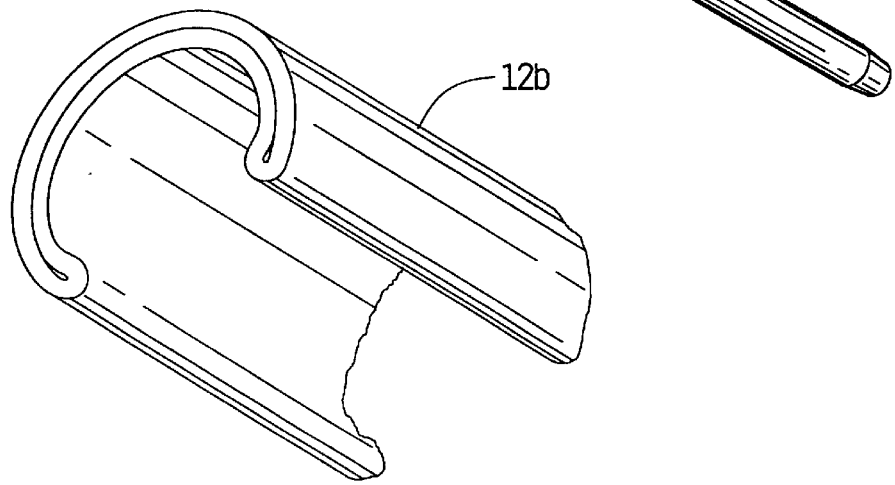
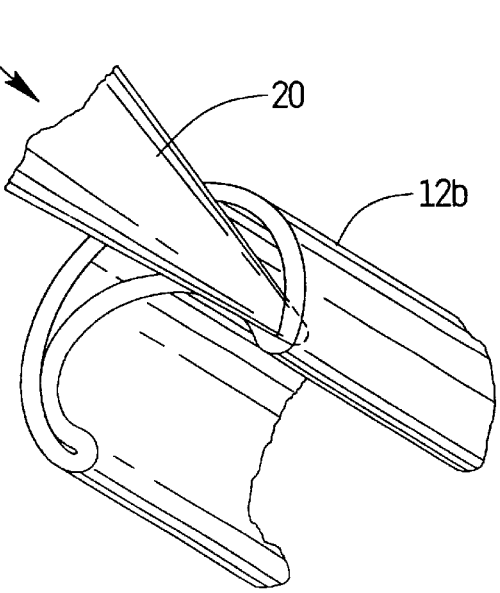

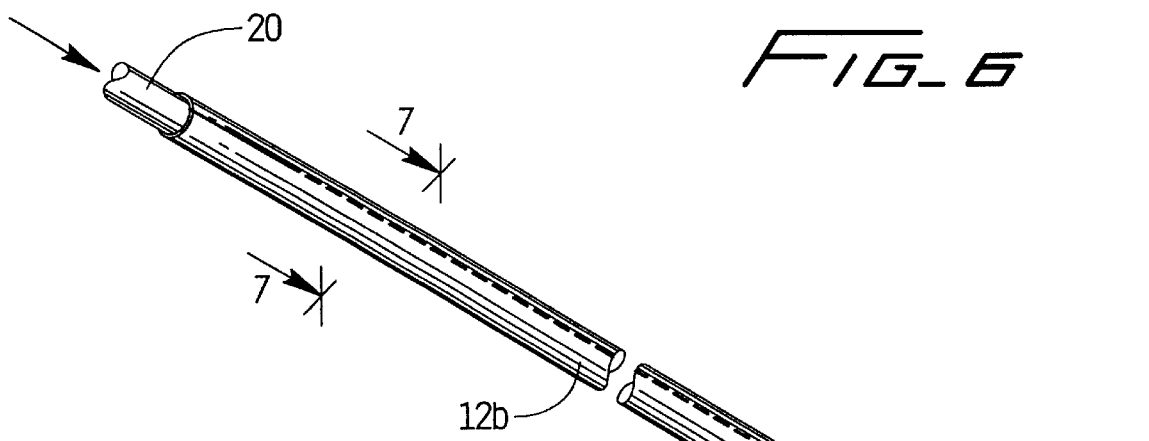
FIG_6
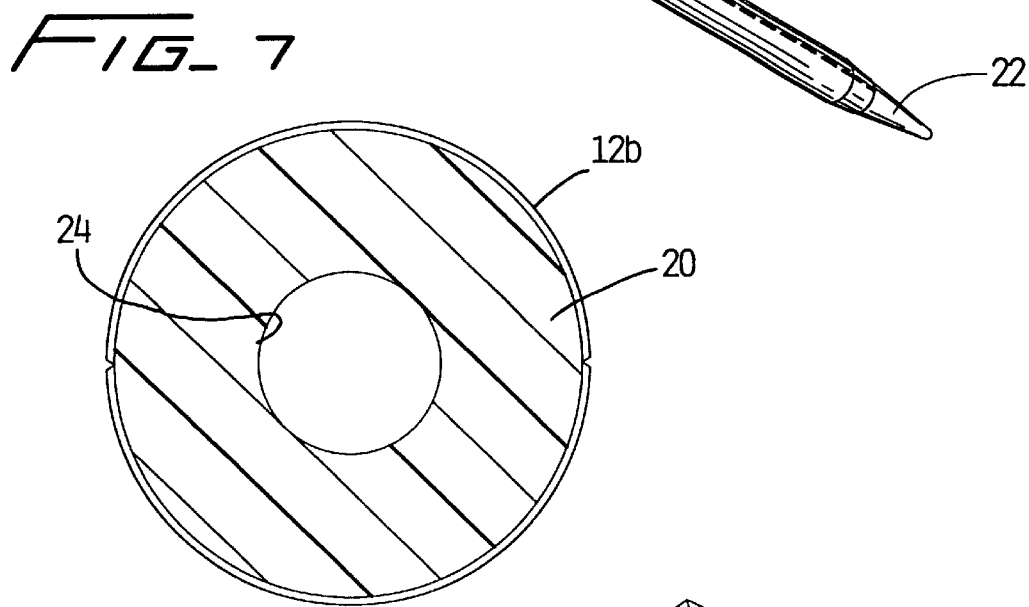
FIG_7
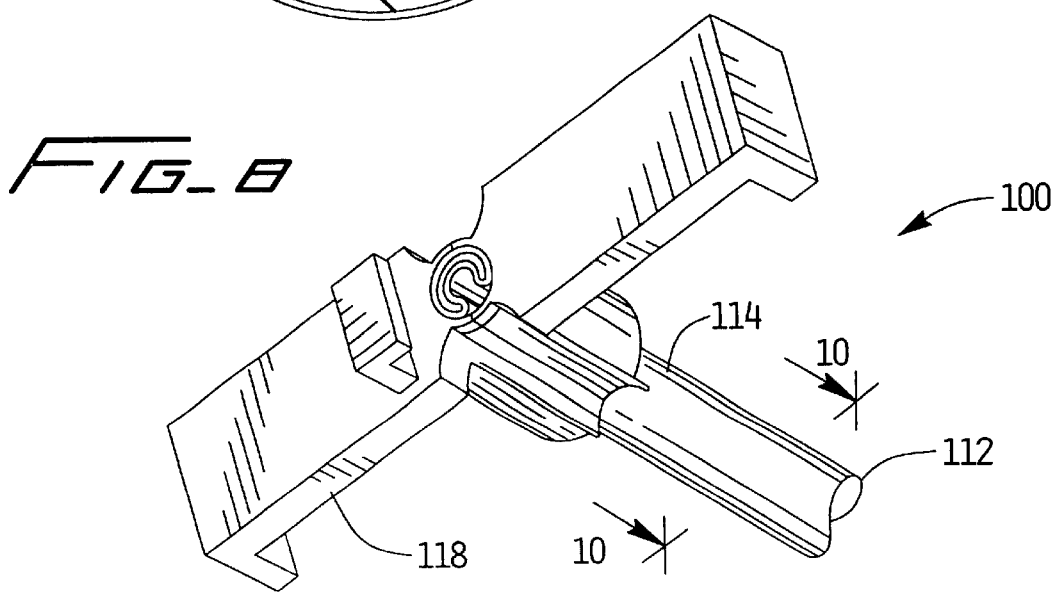
FIG_8

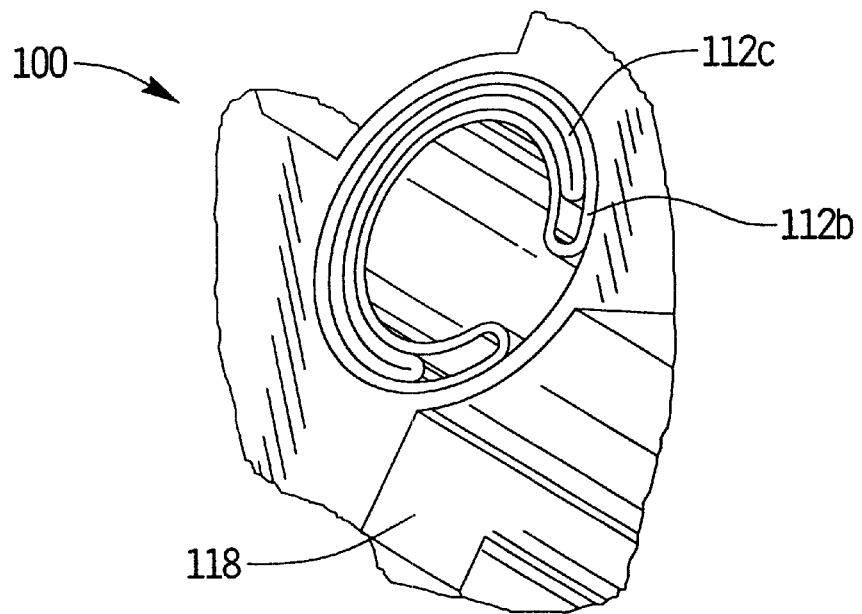
FIG_9
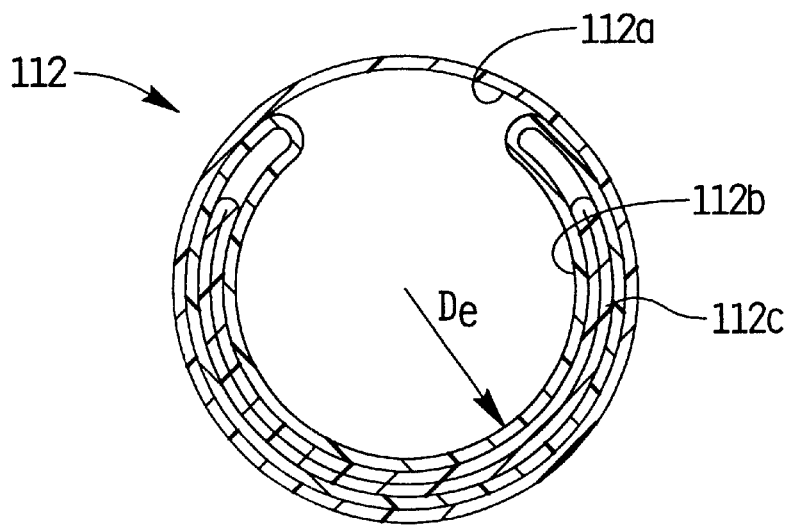
FIG_10

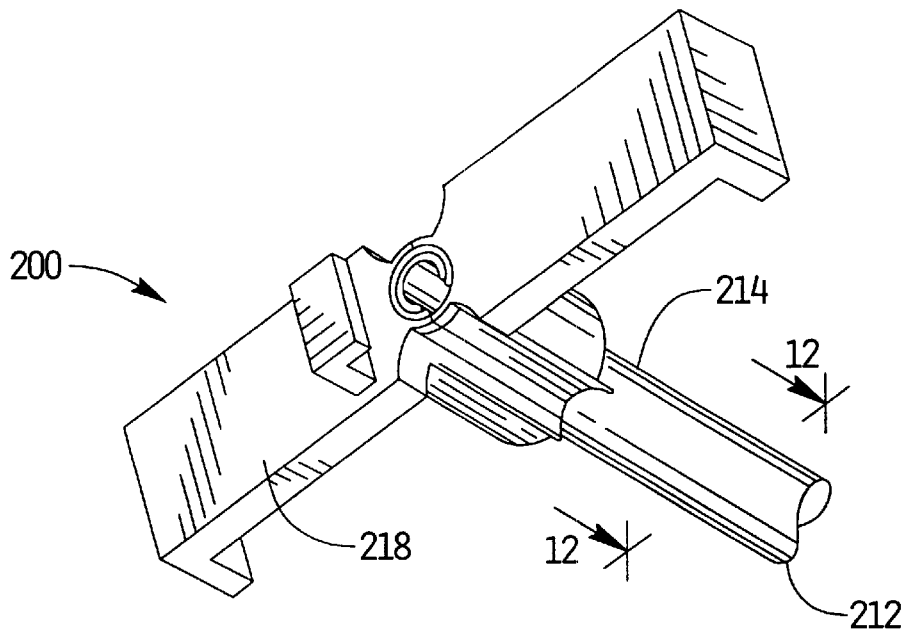
FIG_11
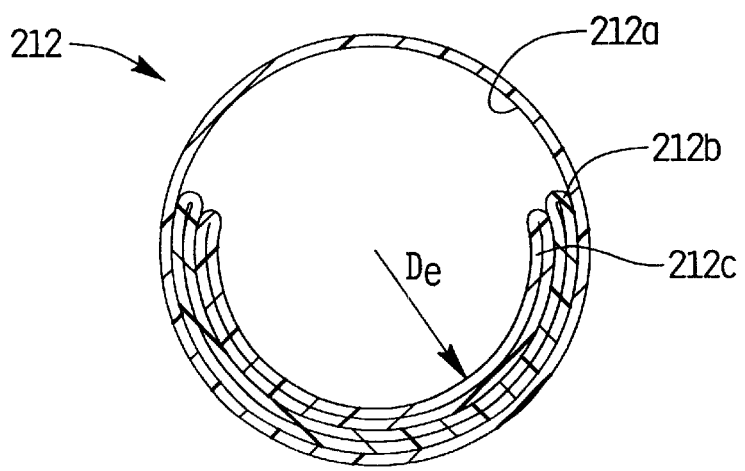
FIG_12

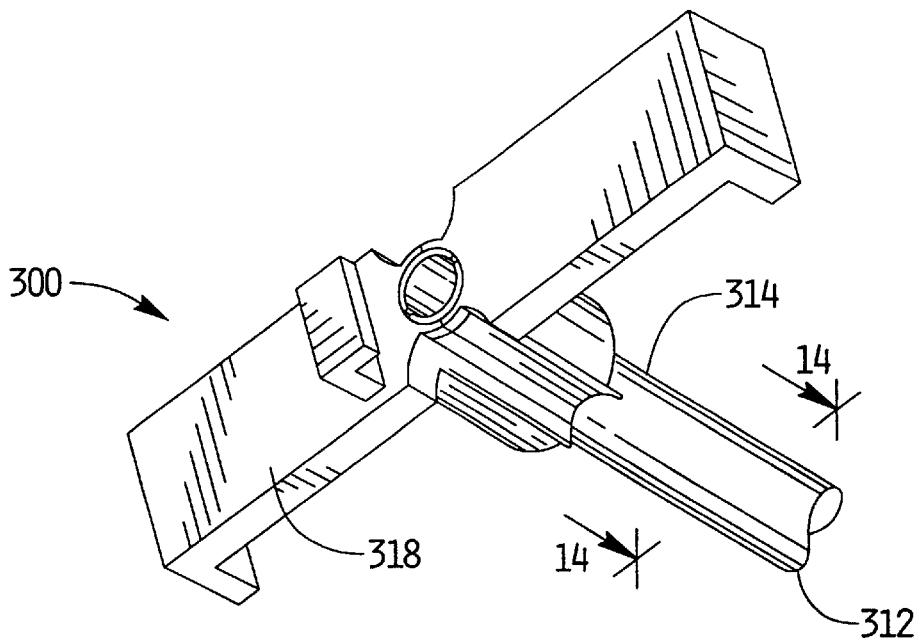
FIG_13
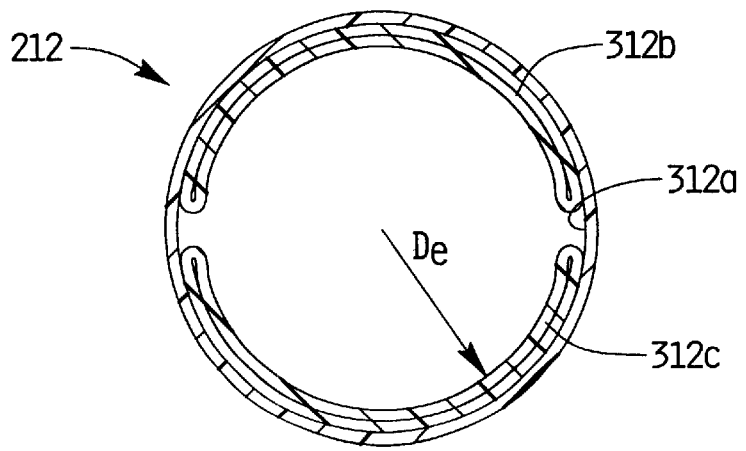
FIG_14

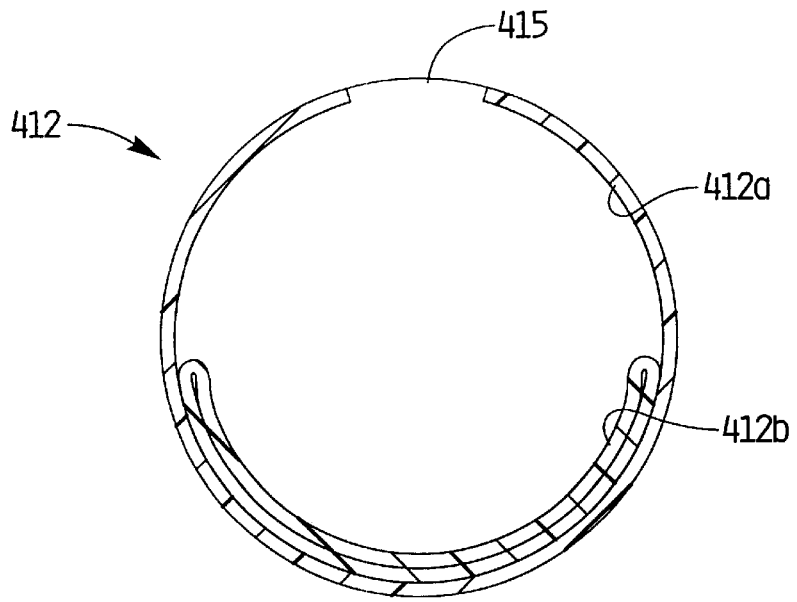
FIG_15
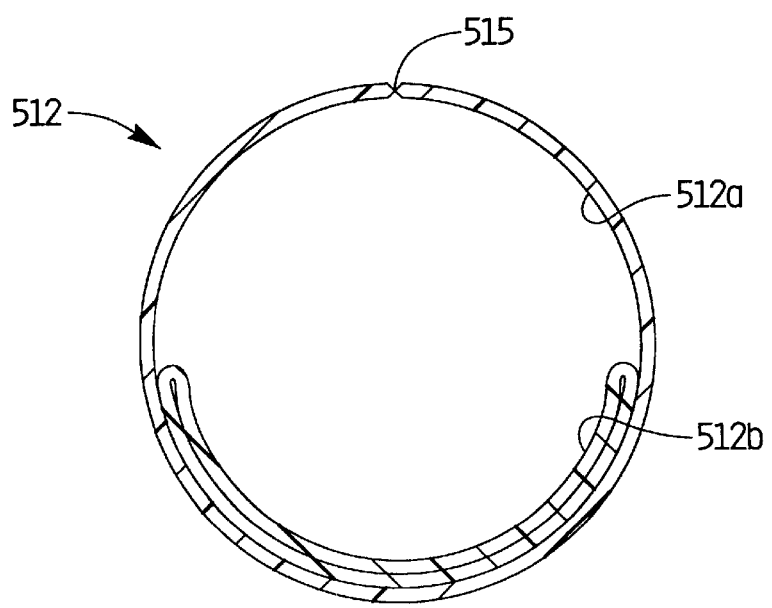
FIG_16 though the interior lumen of the secondary sheath to move the secondary sheath into an open condition, and introducing a second surgical device to the desired position within the blood vessel through the interior lumen of the secondary sheath.

INTRODUCER WITH MULTIPLE SHEATHS AND METHOD OF USE THEREFOR

BACKGROUND OF THE INVENTION

1. Field of the Invention

The subject invention relates to a vascular introducer, and more particularly, to an introducer having multiple sheaths to facilitate sequential placement of multiple diagnostic or therapeutic surgical devices into a blood vessel.

2. Background of the Related Art

Devices for assisting the percutaneous introduction of diagnostic or therapeutic devices into the body are well known in the art. A particularly useful prior art vascular introducer is disclosed in U.S. Pat. No. 4,687,469 to Osypka. This device, which is designed to facilitate the percutaneous introduction of pacemaker electrodes and cardiovascular catheters, includes a thin-walled sheath configured to be slit open with a cutting blade for easy withdrawal.

During a surgical procedure, such as the implantation of a pacemaker electrode or defibrillation lead, it is often necessary to introduce more than one diagnostic or therapeutic device into the body. For example, it is may be necessary to introduce two or more pacemaker electrodes and a cardiovascular catheter during the same procedure. In such an instance, when using either of the prior art vascular introducers described hereinabove, after the introducer sheath has been pealed-away or slit open and withdrawn from the puncture site, a second introducer must be percutaneously advanced into the desired area to facilitate the introduction of a second medial device. This can cause undue trauma to the blood vessel.

It would be beneficial therefore, to provide a vascular introducer configured to facilitate the placement of more than one diagnostic or therapeutic device into the body during a surgical procedure.

SUMMARY OF THE INVENTION

The subject invention is directed to a vascular introducer that is adapted and configured to facilitate percutaneous placement of several diagnostic or therapeutic surgical devices into a blood vessel during a surgical procedure, including, for example, a pacemaker lead and a cardiovascular catheter, or two or more pacemaker leads. The introducer includes an elongated primary sheath defining an interior lumen and having opposed proximal and distal end portions, and at least an elongated secondary sheath disposed within the interior lumen of the primary sheath. The secondary sheath is adapted for movement from a collapsed condition, wherein the sheath assumes a generally arcuate or concave configuration, to an open condition in response to insertion of a dilator through an interior lumen thereof.

The introducer may further comprise an elongated tertiary sheath that can be disposed within the interior lumen of the primary sheath or within the interior lumen of the secondary sheath. Those skilled in the art will readily appreciate that the introducer of the subject invention can be provided with more than three sheaths, as the wall thickness of each sheath is relatively thin. It is envisioned that the interior lumen of each sheath can have a different (i.e., smaller and larger) or similar diameter so as to accommodate different or similar surgical devices.

In a preferred embodiment of the subject invention, the vascular introducer includes an elongated primary sheath defining an interior lumen and having opposed proximal and distal end portions, at least an elongated secondary sheath disposed within the interior lumen of the primary sheath and adapted for movement from a collapsed condition to an open condition, and an elongated dilator configured for reception within the interior lumen of the primary sheath and adapted for insertion through the interior lumen of the secondary sheath to effectuate movement of the secondary sheath from the collapsed condition to the open condition.

Preferably, the dilator has an elongated lumen extending therethrough for receiving an elongated guidewire and a luer-lock adapter may be provided at a proximal end of the dialator. Preferably, a T-shaped griping structure is operatively associated with the proximal end portion of the primary sheath, and the primary sheath includes diametrically opposed elongated score lines, or a similar frangible structure associated therewith, to facilitate separation of the primary sheath from the secondary sheath, and withdrawal of the primary sheath from the surgical site.

The subject invention is also directed to a method of implanting surgical devices through the surface of the skin. The method includes the initial step of providing a vascular introducer including an elongated primary sheath defining an interior lumen, an elongated secondary sheath disposed within the interior lumen of the primary sheath in a collapsed condition, and an elongated dilator disposed within the interior lumen of the primary sheath, where the lumen of the secondary sheath can have, in an expanded condition, a larger diameter than the lumen of the primary sheath. The method further includes the step of advancing the vascular introducer through the surface of, the skin to a desired position within a blood vessel, removing the dilator from the interior lumen of the primary sheath and introducing a first surgical device to the desired position within the blood vessel through the interior lumen of the primary sheath. The method further includes the step of separating the primary sheath from the secondary sheath, advancing the dilator through the interior lumen of the secondary sheath to move the secondary sheath into an open condition, and introducing a second surgical device to the desired position within the blood vessel through the interior lumen of the secondary sheath.

The method further comprises the steps of percutaneously inserting a cannulated needle into the desired area within the blood vessel, verifying the position of the needle under fluoroscopy and by observing fluid return, inserting a guidewire through the needle and into a desired area within the blood vessel and withdrawing the needle from the desired area. The method also includes the steps of threading the dilator over the guidewire to advance the vascular introducer to the desired area within the blood vessel, and then separating or displacing the primary sheath from the secondary sheath.

These and other unique features of the vascular introducer of the subject invention and the method of utilizing the same will become more readily apparent from the following description of the drawings taken in conjunction with the detailed of the preferred embodiments.

BRIEF DESCRIPTION OF THE DRAWINGS

So that those having ordinary skill in the art to which the subject invention appertains will more readily understand how to construct and use the vascular introducer of the subject invention, reference may be had to the drawings wherein:

FIG. 1 is a perspective view of a multi-sheath vascular introducer constructed in accordance with a preferred embodiment of the subject invention;

FIG. 2 is a cross-sectional view taken along line 2—2 of FIG. 1 illustrating the inner sheath of the introducer in a collapsed condition within the outer sheath of the introducer wherein the inner sheath assumes a generally arcuate configuration;

FIG. 3 is a perspective view of the vascular introducer of FIG. 1 with the outer sheath partially peeled away to reveal the inner sheath in a collapsed condition;

FIG. 4 is a perspective view of the proximal portion of the inner sheath in a collapsed arcuate condition;

FIG. 5 is a perspective view of the proximal portion of the inner sheath illustrating the manner by which the inner sheath of the vascular introducer is moved to an open tubular condition from a collapsed arcuate configuration by introducing a dilator into the lumen thereof;

FIG. 6 is a perspective view of the dilator extending through the lumen of the inner sheath of the vascular introducer of FIG. 1;

FIG. 7 is a cross-sectional view taken along line 7—7 of FIG. 6 illustrating the diametrically opposed score lines of the inner sheath for facilitating the separation of the sheath;

FIG. 8 is a perspective view of the proximal end portion of another multi-lumen vascular introducer constructed in accordance with a preferred embodiment of the subject invention which includes first and second nested inner sheaths of different diameter disposed within an outer sheath;

FIG. 9 is an enlarged perspective view of a portion of the proximal end of the vascular introducer of FIG. 8 illustrating the nested inner sheaths thereof in a collapsed condition;

FIG. 10 is a cross-sectional view taken along line 10—10 of FIG. 8 illustrating the relationship of the nested inner sheaths within the outer sheath;

FIG. 11 is a perspective view of the proximal end portion of another multi-sheath vascular introducer constructed in accordance with a preferred embodiment of the subject invention which includes first and second overlaid inner sheaths of different diameter disposed within an outer sheath;

FIG. 12 is a cross-sectional view taken along line 12—12 of FIG. 11 illustrating the relationship of the overlaid inner sheaths within the outer sheath;

FIG. 13 is a perspective view of the proximal end portion of another multi-sheath vascular introducer constructed in accordance with a preferred embodiment of the subject invention which includes first and second inner sheaths of similar diameter in diametrically opposed orientation within an outer sheath;

FIG. 14 is a cross-sectional view taken along line 14–14 of FIG. 13 illustrating the relationship of the diametrically opposed inner sheaths within the outer sheath;

FIG. 15 is an end view of another multi-sheath introducer constructed in accordance with a preferred embodiment of the subject invention which includes a frangible layer of material connecting adjacent edges of the outer sheath; and FIG. 16 is an end view of another multi-sheath introducer constructed in accordance with a preferred embodiment of the subject invention wherein adjacent edges of the outer sheath are secured to one another by a frangible weldment.

These and other features of the introducer assembly of the subject invention will become more readily apparent to those having ordinary skill in the art form the following detailed description of the preferred embodiments.

DESCRIPTION OF THE PREFERRED EMBODIMENTS

In the description which follows the term "proximal" refers to the end of the vascular introducer which is farthest from the surgical site, while the term "Idistal" refers to the end of the device which is nearest to the surgical site. In addition, the phrase "outer sheath" is used interchangeably with the term "primary sheath," the phrases "secondary sheath" and "tertiary sheath" are used interchangeably with the terms "first inner sheath" and "second inner sheath," respectively.

Referring now to the drawings wherein like reference numerals identify similar structural elements of the subject invention, there is illustrated in FIG. 1 a multi-sheath vascular introducer constructed in accordance with a preferred embodiment of the subject invention and designated generally by reference numeral 10.

Vascular introducer 10 includes an elongated tubular body 12 defining opposed proximal and distal end portions 14 and 16. A T-shaped handle assembly 18 is operatively associated with the proximal end 14 of body 12 and the distal end 16 of body 12 is tapered to facilitate percutaneous introduction of the device. As best seen in FIG. 2, the body 12 of vascular introducer 10 is includes an outer (primary) tubular sheath 12a and an inner (secondary) sheath 12b. The inner sheath 12b is disposed in a collapsed condition within the outer sheath 12a. In the collapsed condition, the inner sheath 12b assumes an arcuate or concave configuration. The wall thickness "t" of the outer sheath, 12a and the inner sheath 12b are substantially similar.

In accordance with the subject invention, the outer sheath 12a is configured for introduction of a first surgical device into a blood vessel, such as, for example a pacemaker lead, and the second sheath 12b is configured for the subsequent introduction of a second surgical instrument into the same blood vessel, such as, for example, a cardiovascular catheter or a second pacemaker lead.

Those skilled in the art will readily appreciate that the inner diameter of the lumen of the outer sheath 12a may be different than the inner diameter of the lumen of the inner sheath 12b. This will accommodate surgical instruments of different outer diameter. Thus, the inner diameter of the lumen of outer sheath 12a may be equal to, greater than or less than the inner diameter of the lumen of inner sheath 12b. It should be appreciated that when the inner sheath 12b is in the collapsed state, it does not interfere with the introduction of the first surgical instrument through the lumen of the outer sheath 12a. However, it should also be recognized that the effective inner diameter of the outer sheath 12a is limited by the doubled wall thickness of the collapsed inner sheath 12b disposed within the lumen of outer sheath 12a as shown by radius $D_e$.

Referring now to FIG. 3, the outer sheath 12a of the vascular introducer 10 is configured to be peeled away and separated from the inner sheath 12b in a conventional manner, by providing, for example, diametrically opposed scorelines along the length of the outer sheath. This concepts is well known in the art, as illustrated for example in U.S. Pat. No. 4,512,351 to Pohndorf, and is effectuated by grasping the opposed portions of the T-shaped gripping handle 18 and pulling them apart from one another in the direction indicated by the arrows along the entire length of the body 12. Alternatively, the outer sheath 12a may be cut away from the inner sheath 12b using a tool such as that which is described in U.S. Pat. No. 4,687,469. Once the outer (primary) sheath 12a has been peeled away, the inner (secondary) sheath 12b is revealed in a collapsed position, as illustrated in FIG. 4.

Subsequently, as shown in FIG. 5, a dilator 20 having an outer diameter that is approximately equal to the inner diameter of the interior lumen of the inner sheath 12b (see FIG. 7) is inserted into the interior lumen of the inner sheath 12b. Then, as illustrated in FIG. 6, the dilator 20 (or a dilator sized to correspond to the lumen of the inner sheath) is extended through the interior lumen of the inner sheath 12b to open the lumen. Dilator 20 is then removed from the sheath to permit the introduction of the second surgical instrument therethrough. Dilator 20 is of conventional configuration and generally includes a tapered distal end portion 22 for ease of introduction and a central lumen 24 for receiving a guidewire therethrough, which will be discussed in greater detail hereinbelow.

Referring now to FIG. 8, there is disclosed another vascular introducer constructed in accordance with a preferred embodiment of the subject invention and designated generally by reference numeral 100. Vascular introducer 100 includes an elongated tubular body 112 having opposed proximal and distal end portions, the proximal end portion 114 having a T-shaped handle assembly 118 associated therewith. As best seen in FIGS. 9 and 10, tubular body 112 includes an outer (primary) sheath 112a, a first inner (secondary) sheath 112b disposed within the outer sheath 112a in a collapsed condition, and a second inner (tertiary) sheath 112c nested within the interior lumen of the first inner sheath 112b. In this embodiment, the effective inner diameter of the outer sheath 112a is limited by the combined wall thickness (4t) of the collapsed nested inner sheaths 112b and 112c as shown by radius $D_e$.

The inner diameter of the lumen of each of the sheaths 112a, 112b and 112c may be equal to one another, or they may vary from one to the other depending upon the intended use of the introducer. For example, the inner diameter of the lumen of the first interior sheath 112b may be greater than the inner diameter of the lumen of the outer sheath 112a, while the inner diameter of the second inner sheath 112c may be less than the inner diameter of the lumen of the first inner sheath 112b. It is envisioned that the order in which the sheaths are disposed relative to one another can be set in accordance with the order in which surgical instrumentation is introduced into a blood vessel during a particular surgical procedure. Thus, in accordance with the subject invention, there would be an introducer with a particular sheath arrangement which would correspond to, a given surgical procedure. For example, in pediatric surgical procedures where the blood vessels of the patient are relatively small, it would be beneficial to begin the procedure with an introducer having an outer sheath that is relatively small in diameter, and then sequentially increase the size of the subsequent sheaths so as to prevent undue trauma to the blood vessel.

In operation, as in the case of vascular introducer 10, after the outer sheath 112a has been used for the introduction of a first surgical device, it may be peeled away and separated from the two inner sheaths 112b and 112c in a manner similar to that shown in FIG. 3, by pulling apart the opposed portions of the T-shaped handle 118 so that the outer sheath 112a separates along its length into two parts. Then, the first inner sheath 112b may be opened by extending a dilator therethrough, which would be subsequently removed to facilitate the introduction of a second surgical device therethrough. When the first inner sheath 112b is no longer needed, it may be displaced from the second inner sheath 112c by peeling it into two parts along weakened score lines, or by slitting it along its length using a cutting tool such as that which is disclosed in U.S. Pat. No. 4,687,469 to Osypka, the disclosure of which is herein incorporated by reference in its entirety.

Referring now to FIG. 11, there is disclosed another vascular introducer constructed in accordance with a preferred embodiment of the subject invention and designated generally by reference numeral 200. Vascular introducer 200 includes an elongated body 212 having opposed proximal and distal end portions, the proximal end portion 214 having a T-shaped handle assembly 218 associated therewith. As best seen in FIG. 12, tubular body 212 includes an outer (primary) sheath 212a, a first inner (secondary) sheath 212b disposed within the outer sheath 212a in a collapsed condition, and a second inner (tertiary) sheath 212c overlaying the first inner sheath 212b in a collapsed condition. In this embodiment, the effective inner diameter of the outer sheath 212a is limited by the combined wall thickness (4t) of the collapsed overlying inner sheaths 212b and 212c disposed within the lumen of outer sheath 212a as shown by radius $D_e$. As in the previous embodiment, the inner diameter of the lumen of each of the sheaths 212a, 212b and 212c may be equal to one another, or they may vary from one to the other depending upon the intended use of the introducer.

In use, as in the previous embodiments, after an instrument has been introduced through the outer sheath 212a of vascular introducer 200, the outer sheath may be peeled away and separated from the two overlaid inner sheaths 212b and 212c by pulling apart the opposed portions of the T-shaped handle 218 so that the outer sheath 212a separates along its length into two parts. Then, the first inner sheath 212b may be opened by extending a dilator therethrough, which would be subsequently removed to facilitate the introduction of a second surgical instrument therethrough. When the first inner sheath 212b is no longer needed, it may be removed by peeling it into two parts along weakened score lines, or by slitting it along its length using a cutting tool. Thereafter, the second inner sheath 212c may be opened by extending a dilator therethrough, which would be subsequently removed to facilitate the introduction of a third surgical instrument therethrough.

Although the embodiments of the multi-lumen vascular introducer illustrated in FIGS. 8 and 11 include only two collapsed inner sheaths, it is envisioned and well within the scope of the subject disclosure that the vascular introducer could include more than two overlayed or nested inner sheaths. The more inner sheaths there are however, the greater will be the combined wall thickness of the inner sheaths and thus, the smaller will be the effective inner diameter of the lumen of the outer sheath.

Referring now to FIG. 13, there is disclosed another vascular introducer constructed in accordance with a preferred embodiment of the subject invention and designated generally by reference numeral 300. Vascular introducer 300 includes an elongated body 312 having opposed proximal and distal end portions, the proximal end portion 314 having a T-shaped handle assembly 318 associated therewith. As best seen in FIG. 14, tubular body 312 includes an outer sheath 312a, a first inner sheath 312b disposed within the outer sheath 312a in a collapsed condition, and a second inner sheath 312c diametrically opposed to the first inner sheath 312b in a collapsed condition.

In this embodiment although there are two collapsed inner sheaths 312b and 312c within outer sheath 312a, the effective inner diameter of the outer sheath 312a is greater than the effective inner diameter of the outer sheaths of the embodiments of FIGS. 8 and 11, as shown by the radius $D_e$ in each embodiment. This is because the wall thickness (2t) of the two collapsed inner sheaths 312b and 312c provide an individual effect on the interior lumen of the outer sheath rather than a combined effect, as they are neither overlaid or nested as in the previous embodiments. It is envisioned that more than two interior sheaths may be arranged in the manner illustrated in FIG. 14. For example, there may be two overlaid inner sheaths on either side of the horizontal axis of the outer sheath. Thus, the vascular introducer could provide access to as many as five different devices during a surgical procedure. As in the previous embodiments of the invention, the inner diameter of the lumen of each of the sheaths of the vascular introducer can differ from one another to accommodate different types of devices.

Referring now to FIGS. 15 and 16, there are illustrated, in cross-section, the body portions of two other embodiments of the vascular introducer of the subject invention, designated respectively by reference numerals 412 and 512. Body portion 412 includes an outer sheath 412a and an inner sheath 412b disposed in a collapsed state. The outer sheath 412a of body portion 412 is slit along its length and includes a thin film of frangible material 415, such as Teflon® which connects the opposed edges of the outer sheath 412a. In use, to displace the outer sheath 412a from the inner sheath 412b, the thin film of frangible material 415 is severed, either manually or with a cutting tool, and the outer sheath 412a is removed to reveal the inner sheath 412b. Similarly, the body portion 512 includes an outer sheath 512a and an inner sheath 512b disposed in a collapsed condition. The outer sheath 512a of body portion 512 is also slit along its length and the edges are attached to one another by a weldment 515 which may be severed with little effort to displace the outer sheath 512a from the inner sheath 512b during a surgical procedure.

The subject invention is also directed to a method of implanting surgical devices through the surface of the skin. The method includes the initial step of providing a vascular introducer, such as for example, the vascular introducer 10 of FIG. 1, which includes a tubular body 12 having an elongated primary (outer) sheath 12a defining an interior lumen, an elongated secondary (inner) sheath 12b disposed within the interior lumen of the primary outer sheath in a collapsed condition, and an elongated dilator 20 disposed within the interior lumen of the primary sheath 12a. The method further includes the step of advancing the vascular introducer 10 through the surface of the skin to a desired position within a blood vessel, removing the dilator 20 from the interior lumen of the primary sheath 12a and introducing a first surgical device (not shown) to the desired position within the blood vessel through the interior lumen of the primary sheath 12a.

The method further includes the step of separating the primary sheath 12a from the secondary sheath 12b, as shown for example in FIG. 3, advancing the dilator 20 through the interior lumen of the secondary sheath 12b to move the secondary sheath 12b into an open condition, as shown for example in FIGS. 5 and 6, and introducing a second surgical device (not shown) to the desired position within the blood vessel, through the interior lumen of the secondary sheath 12b after the dilator has been removed therefrom.

The method also includes the steps of percutaneously inserting a cannulated needle into the desired area within the blood vessel, verifying the position of the needle under fluoroscopy and by observing fluid return, inserting a guidewire through the bore of the needle and into the desired area within the blood vessel, and then withdrawing the needle from the desired area. The method further includes the step of threading the dilator 20 over the guidewire by passing it through the central bore 24 to advance the vascular introducer 10 to the desired area within the blood vessel.

Although the disclosed apparatus has been described with respect to preferred embodiments, it is apparent that modifications and changes can be made thereto without departing from the spirit and scope of the invention as defined by the appended claims.

What is claimed is:

1. A vascular introducer comprising:
    a) an elongated primary sheath defining an interior lumen and having opposed proximal and distal end portions; and
    b) at least one additional elongated sheath disposed within the interior lumen of the primary sheath, separate from the primary sheath and from any other sheath and adapted for movement from a collapsed condition to an open condition.

2. A vascular introducer as recited in claim 1, wherein two additional sheaths are disposed within the interior lumen of the primary sheath separate from the primary sheath and from one another.

3. A vascular introducer as recited in claim 2, wherein the two additional sheaths are disposed in an overlaid orientation within the interior lumen of the primary sheath.

4. A vascular introducer as recited in claim 2, wherein the two additional sheaths are disposed in a diametrically opposed orientation within the interior lumen of the primary sheath.

5. A vascular introducer as recited in claim 2, wherein one additional sheath is disposed within an interior lumen of the other additional sheath.

6. A vascular introducer as recited in claim 1, wherein the interior lumen of the primary sheath has a greater diameter than an interior lumen of the at least one additional sheath.

7. A vascular introducer as recited in claim 1, wherein the interior lumen of the primary sheath has a lesser diameter than an interior lumen of the at least one additional sheath.

8. A vascular introducer as recited in claim 1, wherein the interior lumen of the primary sheath and an interior lumen of the at least one additional sheath are equal in diameter.

9. A vascular introducer as recited in claim 2, wherein an interior lumen of one additional sheath has a greater diameter than an interior lumen of the other additional sheath.

10. A vascular introducer as recited in claim 2, wherein an interior lumen of one additional sheath has a lesser diameter than an interior lumen of the other additional sheath.

11. A vascular introducer as recited in claim 2, wherein an interior lumen of one additional sheath and an interior lumen of the other additional sheath are equal in diameter.

12. A vascular introducer as recited in claim 1, wherein at least the distal end portion of the primary sheath is inwardly tapered.

13. A vascular introducer as recited in claim 1, further comprising a T-shaped griping structure operatively associated with the proximal end portion of the primary sheath.

14. A vascular introducer as recited in claim 1, wherein the primary sheath includes means for pealing away the primary sheath from the at least one additional sheath.

15. A vascular introducer as recited in claim 14, wherein the means for peeling away the primary sheath from the at least one additional sheath includes an elongated score line formed in the primary sheath.

16. A vascular introducer as recited in claim 14, wherein the means for peeling away the primary sheath from the at least one additional sheath includes a thin film of frangible material connecting adjacent longitudinal edges of the primary sheath.

17. A vascular introducer as recited in claim 14, wherein the means for peeling away the primary sheath from the at least one additional sheath includes a frangible weldment connecting adjacent longitudinal edges of the primary sheath.

18. A vascular introducer comprising:
a) an elongated primary sheath defining an interior lumen and having opposed proximal and distal end portions;
b) an elongated secondary sheath disposed within the interior lumen of the primary sheath, separate from the primary sheath and from any other sheath and adapted for movement from a collapsed condition to an open condition; and
c) an elongated dilator configured for reception within the interior lumen of the primary sheath and adapted for insertion through the interior lumen of the secondary sheath to effectuate movement of the secondary sheath from the collapsed condition to the open condition.

19. A vascular introducer as recited in claim 18, wherein the dilator has an elongated lumen extending therethrough for receiving an elongated guidewire.

20. A vascular introducer as recited in claim 18, wherein the dilator has tapered distal end portion.

21. A vascular introducer as recited in claim 18, wherein at least the distal end portion of the primary sheath is tapered.

22. A vascular introducer as recited in claim 18, further comprising a T-shaped griping structure operatively associated with the proximal end portion of the primary sheath.

23. A vascular introducer as recited in claim 18, wherein the primary sheath includes means for peeling away the primary sheath from the secondary sheath.

24. A vascular introducer as recited in claim 23, wherein the means for peeling away the primary sheath from the secondary sheath includes an elongated score line formed in a sheath.

25. A vascular introducer as recited in claim 23, wherein the means for peeling away the primary sheath from the secondary sheath includes a thin film of frangible material connecting adjacent edges of a sheath.

26. A vascular introducer as recited in claim 23, wherein the means for facilitating separation from one another includes a frangible weldment connecting adjacent edges of a sheath.

27. A vascular introducer as recited in claim 23, wherein the interior lumen of the primary sheath has a greater diameter than the interior lumen of the secondary sheath.

28. A vascular introducer as recited in claim 23, wherein the interior lumen of the primary sheath has a lesser diameter than the interior lumen of the secondary sheath.

29. A vascular introducer as recited in claim 23, wherein the interior lumen of the primary sheath and the interior lumen of the secondary sheath are of equal diameter.

30. A method of implanting surgical devices through the surface of the skin comprising the steps of:
a) providing a vascular introducer including an elongated primary sheath defining an interior lumen, an elongated secondary sheath separate from the primary sheath and from any other sheath and disposed within the interior lumen of the primary sheath in a collapsed condition, and an elongated dilator disposed within the interior lumen of the primary sheath;
b) advancing the vascular introducer through the surface of the skin to a desired position within a blood vessel;
c) removing the dilator from the interior lumen of the primary sheath;
d) introducing a first surgical device to the desired position within the blood vessel through the interior lumen of the primary sheath;
e) peeling the primary sheath away from the secondary sheath;
f) advancing the dilator through the interior lumen of the secondary sheath to move the secondary sheath into an open condition; and
g) introducing a second surgical device to the desired position within the blood vessel through the interior lumen of the secondary sheath.

31. A method according to claim 30, further comprising the step of percutaneously inserting a cannulated needle into the desired area within the blood vessel.

32. A method according to claim 30, further comprising the step of verifying the position of the needle under fluoroscopy and by observing fluid return.

33. A method according to claim 30, further comprising the step of inserting a guidewire through the needle and into the desired area within the blood vessel.

34. A method according to claim 33, further comprising the step of withdrawing the needle from the desired area.

35. A method according to claim 34, further comprising the step of threading the dilator over the guidewire to advance the vascular introducer to the desired area within the blood vessel.

* * * * *